United States Patent [19]

Layton

[11] 4,209,023
[45] Jun. 24, 1980

[54] TISSUE PRESSURE MEASURING DEVICE

[75] Inventor: Terry N. Layton, Arlington Heights, Ill.

[73] Assignee: The Kendall Company, Boston, Mass.

[21] Appl. No.: 13,955

[22] Filed: Feb. 22, 1979

[51] Int. Cl.² ............................................. A61B 5/00
[52] U.S. Cl. .................................................. 128/748
[58] Field of Search ........................ 128/748, 673–675

[56] References Cited

U.S. PATENT DOCUMENTS

| | | | |
|---|---|---|---|
| 2,866,453 | 12/1958 | Jewett | 128/674 |
| 3,662,743 | 5/1972 | Amarante et al. | 128/748 |
| 3,730,168 | 5/1973 | McWhorter | 128/748 |
| 3,920,002 | 11/1975 | Oye et al. | 128/748 |
| 4,170,224 | 10/1979 | Garrett et al. | 128/748 |

*Primary Examiner*—William E. Kamm
*Attorney, Agent, or Firm*—Powell L. Sprunger

[57] ABSTRACT

A tissue pressure measuring device comprising, a hollow needle and a conduit communicating with the needle at a distal end thereof, with the conduit having a lumen and including a transparent portion having a reference marking. The device has a syringe having a plunger, an outer wall defining a chamber, a barrel received in the chamber and defining a cavity to slidably receive the plunger in sealing engagement with an inner surface of the barrel and permit movement of the plunger between inner and outer positions of the plunger relative to the barrel. The chamber and cavity have a combined volume substantially greater than the volume of the cavity, and the plunger has reference indicia disposed along the plunger to determine the position of the plunger relative to a reference position on the syringe. The device has a valve assembly communicating with the conduit lumen and syringe chamber, with the valve assembly selectively establishing communication between the lumen and chamber, and establishing communication between the chamber and the atmosphere while closing the lumen from the chamber.

7 Claims, 3 Drawing Figures

TISSUE PRESSURE MEASURING DEVICE

BACKGROUND OF THE INVENTION

The present invention relates to medical diagnostic devices, and more particularly to tissue pressure measuring devices.

The pressure of closed tissue in a patient is normally either zero or slightly negative. However, injury or trauma to the tissue may cause severance of one or more blood vessels and flow of blood into the tissue. Since the tissue is closed by the fascia surrounding the muscle belly, the blood from the ruptured vessels causes an increase of pressure in the closed tissue compartment. In the event that the tissue pressure should exceed the capillary or perfusion pressure, the collateral blood vessels may become occluded and tissue perfusion ceases. Persistance of this abnormal pressure condition for a period of time may result in ischemia and eventually irreversible tissue damage. However, the pressure condition can be relieved through performance of a fasciotomy procedure, in order to reestablish tissue perfusion. Hence, it is necessary to ascertain the pressure in the closed tissue compartment to determine whether fasciotomy is necessary or desired.

SUMMARY OF THE INVENTION

A principal feature of the present invention is the provision of an improved device of simplified construction for measuring tissue pressure.

The measuring device of the present invention comprises, a hollow needle, a conduit communicating with the needle at a distal end thereof, with the conduit having a lumen and including a transparent portion having a reference marking. The device includes a syringe having a plunger, an outer wall defining a chamber, and a barrel received in the chamber and defining a cavity to slidably receive the plunger in sealing engagement with an inner surface of the barrel and permit movement of the plunger between inner and outer positions of the plunger relative to the barrel. The chamber and cavity have a combined volume substantially greater than the volume of the cavity, and the plunger has reference indicia disposed along the plunger to determine the position of the plunger relative to a reference position on the syringe. The device has valve means communicating with the conduit lumen and syringe chamber, with the valve means selectively establishing communication between the lumen and chamber, and establishing communication between the chamber and the atmosphere while closing the lumen from the chamber.

A feature of the present invention is that the syringe plunger may be utilized to withdraw a testing liquid to the reference marking on the conduit transparent portion while the valve means establishes communication between the chamber and lumen.

Another feature of the invention is that the plunger may then be placed at an outer position as indicated by a null reference indicia on the plunger without displacing the liquid from the reference marking through use of the valve means in the configuration establishing communication between the chamber and atmosphere.

Yet another feature of the invention is that the needle may be placed in closed tissue of a patient and the valve means may be positioned to establish communication between the chamber and lumen preparatory to a determination of pressure in the tissue.

Still another feature of the invention is that the plunger of the syringe may be pressed into the syringe until the liquid is displaced from the reference marking responsive to a pressure in the syringe which exceeds the pressure in the closed tissue.

A feature of the present invention is that the pressure in the syringe chamber and in the closed tissue may be readily determined by the indicia on the syringe plunger.

Thus, a feature of the present invention is that the tissue pressure may be determined in a simplified manner in order to ascertain whether fasciotomy for the patient is necessary or desired.

Further features will become more fully apparent in the following description of the embodiments of this invention and from the appended claims.

DESCRIPTION OF THE PREFERRED EMBODIMENTS

Figure 1:
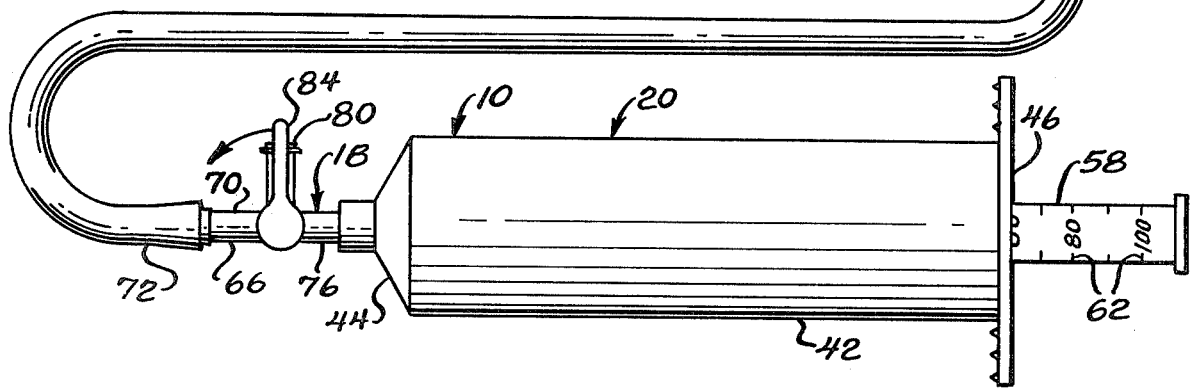
FIG. 1 is a fragmentary elevational view of a tissue pressure measuring device of the present invention.
Figure 2:
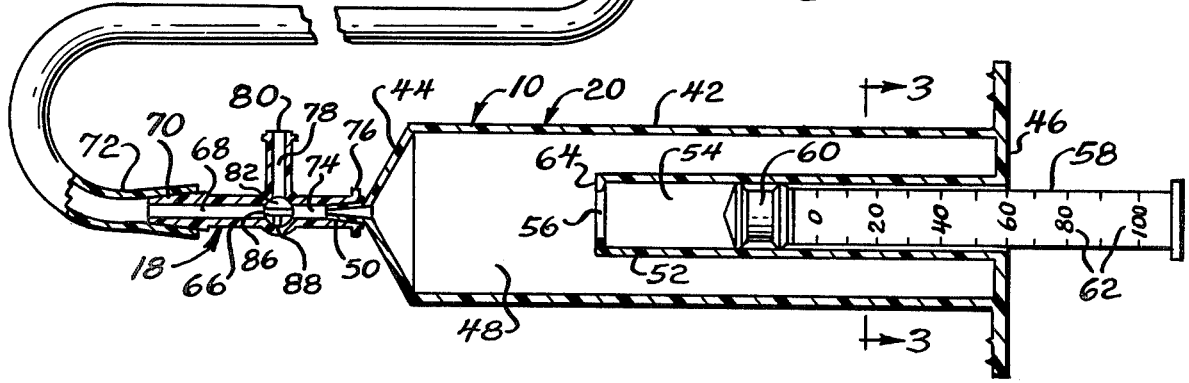
FIG. 2 is a fragmentary elevational view, taken partly in section, of the device of FIG. 1.
Figure 3:
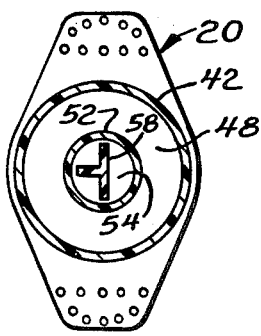
FIG. 3 is a sectional view taken substantially as indicated along the line 3—3 of FIG. 2.

Referring now to FIGS. 1-3, there is shown a tissue pressure measuring device 10 comprising a hollow needle 12, an elongated conduit 14 having a lumen 16, a valve assembly 18, and a syringe 20. The needle 12 has a tip 22 for placement in the tissue of a patient, and a hub 24 to releasably attach the needle 12 to a distal end 26 of the conduit 14 through suitable means, such as an adapter 28 at the distal end 26 of the conduit 14.

The conduit 14 has a reference portion 32 which may be constructed of a suitable transparent plastic or glass material, and in a preferred form is relatively rigid. As shown, the reference portion 32 has an enlarged segment 34 with a transverse reference marking 36 extending at least partially circumferentially around the segment 34 for a purpose which will be described below. The lumen in the segment 34 may approximate or be slightly larger than capillary dimensions, such that an interface of air and liquid is defined by the meniscus as liquid passes into the segment 34. The conduit 14 may have a first tubular section 38 connecting the reference portion 32 to the adapter 28, and a second tubular section 40 of flexible material connecting a proximal end of the reference portion 32 to the valve assembly 18. Of course, the first and second tubular sections 38 and 40 and reference portion 32 may be constructed in a single piece, or the reference portion 32 may be constructed as part of the adapter 28 or the needle 12 itself, if desired.

The syringe 20 has an outer wall 42, a forward wall 44, and a rear wall 46 defining an enlarged chamber 48 communicating with a tip 50 at a distal end of the syringe. The syringe 20 also has an elongated cylindrical barrel 52 extending from the rear wall 46 into the syringe chamber 48, and defining a cavity 54 communicating with the chamber 48 through an opening 56 at a distal end of the barrel 52. As shown, the combined volume of the chamber 48 and cavity 54 is substantially greater than the volume of the cavity 54 itself for a purpose which will be described below. The syringe 20 also has a plunger 58 slidably received in the barrel cavity 54, and having a sealing member 60 of suitable elastic material, such as rubber, at a distal end of the plunger 58 to sealingly engage against an inner surface of the barrel 52. The plunger 58 has reference indicia or markings 62 disposed and spaced along the plunger. The indicia 62 is suitably calibrated in terms of pressure units, such that a pressure determination may be made during use of the device in conjunction with a reference position defined by the rear wall 46, as will be further described below. As shown, the barrel 52 may have an inwardly directed annular flange 64 at the distal end of the barrel 52 in order to limit inner or forward movement of the plunger 58 relative to the barrel 52.

The valve assembly 18 has a housing 66 defining a first passageway 68 communicating with the conduit lumen 16 when a distal end 70 of the housing 66 is received in a proximal end 72 of the conduit 14. The housing 66 also defines a second passageway 74 to receive the syringe tip 50 in a proximal end 76 of the housing 66. The housing 66 also has a third passageway 78 which communicates with the atmosphere through a port 80 at an outer end of the housing 66.

The valve assembly 18 also has a valve element 82 rotatably mounted in the housing 66, and a handle 84 connected to the valve element 82 on the exterior of the housing 66 in order to move the valve element 82 between first and second rotational positions. As shown, the valve element 82 has a first channel 86 extending through the valve element 82, and a second channel 88 communicating between a central portion of the first channel 86 and the exterior of the valve element 82. Thus, the valve element 82 may be rotated through use of the handle 84 between a first position with the first channel 86 communicating between the first and second passageways 68 and 74 while closing the third channel 78, as illustrated in FIGS. 1 and 2, and a second position with the second channel 88 communicating with the second passageway 74 and the first channel 86 communicating with the third passageway 78 while closing the first passageway 68. Accordingly, in the first rotational position of the valve element 82, the valve assembly 18 establishes communication between the lumen 16 of the conduit 14 and the chamber 48 of the syringe 20 while closing the conduit and chamber from the atmosphere. However, in the second rotational position of the valve element 82, the valve assembly 18 establishes communication between the syringe chamber 48 and the atmosphere through the valve element 82 and port 80 while closing the conduit lumen 16 from the atmosphere and the chamber 48.

In use of the device, the syringe plunger 58 is moved to the inner position, the valve element 82 is moved to the first rotational position establishing communication between the syringe chamber 48 and conduit lumen 16, and the tip 22 of the needle 12 is placed in a suitable testing liquid, such as a saline solution. Next, the syringe plunger 58 is withdrawn from the syringe in order to aspirate liquid L into the needle 12 and conduit 14 until the meniscus M of the liquid L reaches the reference marking 36 of the reference portion 32, as may be readily determined through the transparent walls of the reference portion 32, with the enlarged segment 34 enhancing visualization of the meniscus M adjacent the marking 36. At this time, the valve element 82 of the valve assembly 18 is moved to the second rotational position in order to establish communication between the syringe chamber 48 and the atmosphere, and close the conduit lumen 16 from the atmosphere. Next, the plunger 58 of the syringe is withdrawn until the null or zero reference marking of the indicia 62 on the plunger 58 is aligned with the rear wall 46 of the syringe, which is accomplished without displacing the meniscus M of the liquid L relative to the reference marking 36 on the reference portion 32 since the conduit lumen 16 is closed at this time. The needle tip 22 may then be placed in the closed tissue of the patient preparatory to testing.

At this time, the handle 84 of the valve assembly 18 is utilized to move the valve element 82 to the first rotational position, and again establish communication between the conduit lumen 16 and the syringe chamber 48 with the interior of the device closed from the atmosphere. Next, the syringe plunger 58 is slowly pushed into the barrel 52 in order to increase the pressure in the syringe chamber 48 and the conduit lumen 16 while viewing the position of the liquid meniscus M relative to the reference marking 36 on the conduit 14. So long as the pressure in the syringe chamber 48 is less than the tissue pressure, the meniscus M remains in place aligned with the reference marking 36. However, once the pressure in the syringe chamber 48 exceeds the tissue pressure, the liquid L begins to pass through the needle into the tissue, and the meniscus M is displaced distally from the reference marking 36 on the conduit 14. Hence, once the meniscus M of the liquid L begins to move relative to the reference marking 36, the physician ceases forward movement of the syringe plunger 58, and the pressure at which the event takes place may be readily determined by the calibrated indicia 62 as aligned with the rear wall 46 of the syringe 20. Thus, the indicia 62 may be utilized to ascertain the pressure in the chamber 48 and the tissue pressure at the time meniscus M begins to move from the reference marking 36. Since the combined volume of the syringe chamber 48 and the barrel cavity 54 is substantially greater than the volume of the cavity 54 itself, the air is compressed a substantially less amount for a given displacement of the plunger 58 than in a typical syringe. Thus, the syringe plunger 58 must be moved a substantially greater distance than normally required to create the pressures necessary to move the meniscus, such that the chamber 48, syringe barrel 52, and plunger 58 cooperate to magnify the unit of linear plunger displacement per unit of pressure increases, and thus obtain substantially greater accuracy of pressure determination in the tissue.

Thus, in accordance with the present invention, the pressure in closed tissue of a patient may be ascertained in a simplified manner. Further, the pressure determination may be made with improved accuracy due to the structure of the syringe which essentially magnifies the amount of movement required by the syringe plunger to obtain a slight increase of pressure in the syringe. Once the tissue pressure has been determined, the physician may decide whether a fasciotomy procedure is necessary or desired in order to reestablish tissue perfusion.

The foregoing detailed description is given for clearness of understanding only, and no unnecessary limitations should be understood therefrom, as modifications will be obvious to those skilled in the art.

I claim:

1. A tissue pressure measuring device, comprising:
    conduit means defining a lumen comprising a hollow needle at the distal end of the conduit means, a transparent reference portion, and a proximal end;
    pump means comprising a plunger, an elongated barrel defining a cavity to slidably receive said plunger and permit movement of the plunger between inner and outer positions relative to the barrel, means defining a chamber communicating with said cavity and substantially increasing the volume of the pump means relative to the volume displaced in said cavity between said inner and outer positions of the plunger, and means for determining the relative position of the plunger in the cavity between said inner and outer positions; and valve means for selectively establishing communication between the pump means and the lumen adjacent the proximal end of the conduit means, and for closing the lumen from the pump means while permitting pumping of fluid by said pump means.

2. The device of claim 1 wherein said reference portion comprises an enlargement of the conduit means having a reference marking thereon.

3. The device of claim 1 wherein the chamber defining means comprises a wall substantially enclosing said barrel.

4. The device of claim 1 wherein the determining means comprises a plurality of indicia spaced along said plunger.

5. The device of claim 1 wherein the valve means comprises, a housing having a first passageway communicating with the lumen of the conduit means, a second passageway communicating with the chamber of the pump means, and a third passageway communicating with the atmosphere through a port, said valve means further comprising a valve element having channel means and being rotatably mounted in the housing for movement between a first position with the channel means communicating between said first and second passageways while preventing communication of the channel means with the third passageway, and a second position with the channel means communicating between the second and third passageways while preventing communication of the channel means with the first passageway.

6. The device of claim 5 wherein the valve element has first and second channels defining said channel means, said first channel extending through the valve element, and said second channel communicating between said first channel and the outside of the valve element.

7. A tissue pressure measuring device, comprising:
a hollow needle;
a conduit communicating with the needle at a distal end thereof, said conduit having a lumen and including a transparent portion having a reference marking;
a syringe having a plunger, an outer wall defining a chamber, a barrel received in said chamber and defining a cavity communicating with the chamber adjacent a distal end of the barrel, said plunger being slidably received in the barrel cavity with the plunger sealingly engaging against an inner surface of the barrel, said chamber and cavity having a combined volume substantially greater than the volume of the cavity, and said plunger having reference indicia disposed along the plunger to determine the position of the plunger relative to a reference position on the syringe; and
valve means communicating with the conduit lumen and syringe chamber, said valve means selectively establishing communication between said lumen and chamber, and establishing communication between the chamber and the atmosphere while closing the lumen from the chamber.

* * * * *